United States Patent
Huitema et al.

[11] Patent Number: 6,083,237
[45] Date of Patent: Jul. 4, 2000

[54] BIOPSY INSTRUMENT WITH TISSUE PENETRATING SPIRAL

[75] Inventors: Thomas W. Huitema; David K. Gregoire, both of Cincinnati; Michael L. Kruszynski, Loveland; Salvatore Privitera, West Chester; James W. Voegele, Cincinnati, all of Ohio

[73] Assignee: Ethico Endo-Surgery, Inc., Cincinnati, Ohio

[21] Appl. No.: 09/177,779

[22] Filed: Oct. 23, 1998

[51] Int. Cl.[7] .................................................. A61B 17/14
[52] U.S. Cl. ............................................ 606/180; 600/567
[58] Field of Search ................................ 606/170, 167, 606/185, 180; 600/564–567

[56] References Cited

U.S. PATENT DOCUMENTS

| | | |
|---|---|---|
| 2,549,731 | 4/1951 | Wattley . |
| 3,150,379 | 9/1964 | Brown . |
| 4,080,959 | 3/1978 | Leveen ................................... 128/2 H |
| 4,177,797 | 12/1979 | Baylis et al. ........................... 128/754 |
| 4,399,810 | 8/1983 | Samuels et al. ....................... 128/337 |
| 4,407,286 | 10/1983 | Noiles et al. .......................... 128/334 |
| 4,505,273 | 3/1985 | Braun et al. ........................... 128/335 |
| 4,607,638 | 8/1986 | Crainich ................................ 128/335 |
| 4,649,151 | 3/1987 | Dougherty et al. ..................... 514/410 |
| 4,682,606 | 7/1987 | DeCaprio ............................... 128/754 |
| 4,733,664 | 3/1988 | Kirsch et al. .......................... 128/334 |
| 4,762,260 | 8/1988 | Richards et al. ......................... 227/19 |
| 4,874,122 | 10/1989 | Froelich et al. ......................... 227/19 |
| 4,983,176 | 1/1991 | Cushman ................................ 606/151 |
| 5,018,530 | 5/1991 | Rank et al. ............................. 600/567 |
| 5,047,040 | 9/1991 | Simpson et al. ........................ 606/159 |
| 5,078,723 | 1/1992 | Dabce et al. ........................... 606/159 |
| 5,147,307 | 9/1992 | Seymourr ............................... 604/116 |
| 5,192,270 | 3/1993 | Carswell, Jr. ........................... 604/116 |
| 5,197,484 | 3/1993 | Kornberg et al. ....................... 128/754 |
| 5,221,269 | 8/1993 | Miller et al. ............................ 604/281 |
| 5,222,975 | 6/1993 | Crainich ................................ 606/219 |
| 5,240,011 | 8/1993 | Assa ...................................... 128/751 |
| 5,246,156 | 9/1993 | Rothfuss et al. ........................ 227/176 |
| 5,366,479 | 11/1994 | McGarry et al. ........................ 606/219 |
| 5,488,958 | 2/1996 | Topel et al. ............................. 606/180 |
| 5,762,069 | 6/1998 | Kelleher et al. ......................... 606/566 |

FOREIGN PATENT DOCUMENTS

WO9608208A1   3/1996   WIPO .

OTHER PUBLICATIONS

Sandra S. Kramer, M.D. et al. "A Permanent Radiopaque Marker Technique for the Study of Pharyngeal Swallowing in Dogs" Dysphagia 1:163–167 (1987).

*Primary Examiner*—Michael Buiz
*Assistant Examiner*—Kevin Truong
*Attorney, Agent, or Firm*—Matthew S. Goodwin

[57] ABSTRACT

A surgical instrument for excising a targeted tissue mass to be biopsied from adjacent bodily tissue on a surgical patient is disclosed. The instrument has an elongated tube and a tissue penetrating spiral having a spiral lumen therethrough mounted within the elongated tube for rotational movement. When the spiral is rotated, it penetrates distally into the targeted tissue mass. The mass is received in the spiral lumen for subsequent excision of the mass to be biopsied. A large biopsy sample can be obtained because of the ample space within the lumen of the tissue penetrating spiral. Since a large biopsy sample can be taken, the number of samples which need to be taken is minimized, and the consequent trauma to the patient is significantly reduced.

13 Claims, 13 Drawing Sheets

BIOPSY INSTRUMENT WITH TISSUE PENETRATING SPIRAL

BACKGROUND OF INVENTION

This invention relates to an instrument for excising a portion of a suspected lesion which is desired to be biopsied for determination of malignancy. More specifically, it relates to such an instrument which can perform the excision and remove the excised tissue in a minimally invasive manner.

Statistics currently reveal that one in nine American women will develop breast cancer. It is the leading cause of cancer deaths in women between the ages of 40–55, and the second leading cause of cancer deaths in women overall. Unfortunately, breast cancer will only be diagnosed in about one in eight women, and one in thirty will die of this disease. Breast cancer does occur in men but it is much uncommon.

A biopsy of the breast is often indicated if suspicious tissue is detected. Biopsy requests stem from a screening process generally performed via a physical examination to detect a palpable lesion or a mammogram for the detection of a nonpalpable lesion. Five out of six biopsies performed return benign indications.

The goal of the biopsy is the discovery and accurate diagnosis of benignity or malignancy of suspect tissue. Survival rates are significantly greater with early detection. However, as detection is attempted in earlier stages of carcinoma development, accurate sampling of the lesion becomes more difficult due to small lesion size. Ideally, a sufficiently large sample size is taken to accurately diagnosis disease state with minimal trauma (physical deformity or scarring) to the patient.

The current standard for care is a significantly invasive procedure known as "Open Excisional Biopsy". Prior to an open excisional biopsy for a nonpalpable mass, an interventional radiologist will initially take mammograms to place a guidewire which directs the surgeon to the area of excision. Mammograms are then taken to assure that the guidewire is accurately placed in or near the desired biopsy site. The guidewire has a barbed end in order maintain its position at the desired site and is fed through an elongated needle.

The general surgeon applies local or, more commonly, general anesthesia, during an open excisional biopsy. Dissection is made through the skin and subcutaneous fat and the flap is undercut and retracted. Incision length, during an open excisional biopsy generally runs between 2–5 inches and is dependent on the location of the lesion, breast characteristics, and surgeon technique. The breast parenchyma is then dissected along the guidewire until the site of the specimen is exposed. The specimen, generally spherical in shape centered about the barbed end of the guidewire, and roughly 1 inch in diameter, is manually excised.

The specimen size taken during an open excisional biopsy is adequate, however deformation (scarring and subsequent shape of the breast) and potential "seeding" of the cancerous cells is often a large concern. Accuracy is generally acceptable, however the guidewire often moves from its original position during the excisional process leading to decreased accuracy and the need for larger specimens.

New technologies are being developed to assist the early detection of breast cancer. The technologies are primarily focused on imaging of nonpalpable tissue and accessing the tissue with minimally invasive techniques for biopsy. The cost and trauma associated with open excisional biopsy is minimized with these technologies.

The two primary imaging technologies for assisting minimally invasive breast biopsy of a nonpalpable mass are ultrasound and stereotactic X-rays. Ultrasound accurately guides a hand-held core biopsy needle (CBN) to the biopsy site. Stereotactic imaging is performed with the patient lying prone on a stereotactic table and X-rays are taken at 15 degrees off-axis on each side of the breast. The X-rays are fed into a digital signal imaging system to create a 3-D reference; the location for biopsy is triangulated and coordinates are fed to the stereotactic table.

The actual specimen removal in the minimally invasive approach is performed in any one of the following ways.

TruCut® Needle Method—The "TruCut" needle method utilizes a small diameter needle which is inserted to a desired depth, actuated, and removed. The product for practicing this method has two co-axial tubular members. The outer member is retracted exposing a lateral opening in the inner member. The elastic property of the tissue causes tissue to enter the hollow core of the inner member. The outer member is then advanced forward, shearing the tissue sample which has been trapped in the inner member. Inherent disadvantages to this technique are the need for multiple insertions with questionable accuracy and extremely limited tissue sample sizes.

Surface to Site Core Sampling (SSCS)—The SSCS method attempts to maximize accuracy through the increase in sample size while maintaining controlled guidance. A cylindrical cutting tube is advanced through an opening in the skin. As it moves forward, it creates a continuous cylindrical core sample until it reaches the depth desired by the surgeon. Upon completion of the linear motion, the distal end of the sample is transected, and the device is withdrawn with the sample within the cutting element. The critical disadvantage to this approach is the trauma and disfigurement associated with excision of the healthy tissue superior to the site of questionable tissue.

Percutaneous Core Biopsy (PCB)—The PCB method attempts to obtain the advantages of single insertion and large sample size of the SSCS approach, while minimizing disfigurement as achieved by the TruCut® needle method. As in the case of a TruCut® needle device, the PCB has multiple co-axial tubular members. However, one of the members remains stationary, eliminating the need for multiple insertions. Samples are obtained in a controlled contiguous manner which ultimately achieves the desire for obtaining large tissue samples at the questionable site.

Another recent minimally invasive approach for excising a portion of a targeted lesion is described in U.S. Pat. No. 5,526,822. The biopsy apparatus described in this patent has an outer biopsy cannula with a penetrating member for positioning adjacent the targeted lesion. The biopsy cannula has a lateral tissue receiving port, and a vacuum is drawn through the port for pulling tissue into the port. An inner cutting cannula moves forwardly to excise the tissue received in the port. With the aid of a vacuum drawn on the inner cutting cannula, the inner cutting cannula retains the excised tissue as the inner cannula is retracted for tissue removal, and the outer biopsy cannula remains stationary. Following removal, the outer biopsy cannula can be rotated relative to a fixed housing, and multiple samples can therefore be taken circumferentially without the need for multiple insertions and withdrawals of the biopsy cannula. The biopsy apparatus and its method of use as described in the '822 patent are exemplified in the Mammotome® Breast Biopsy System.

In addition to biopsy instruments which contain lateral receiving ports for receiving tissue which is subsequently severed with a cutter, additional mechanisms have been disclosed to excise the tissue from the targeted lesion. For example, U.S. Pat. No. 4,177,797 describes a tissue cutter with a sharp helical thread along a needle which rotates into the tissue. An outer hollow cylindrical cutting tube slides over the needle to cut the tissue. The tissue is trapped between the inner diameter of the cutter and the threaded needle. The excised tissue is then retrieved by removal of the threaded needle and cutting tube simultaneously.

Unfortunately, the sample size obtained is limited because of the limited space between the solid needle and the tissue cutter. A limited sample size requires the user to take significantly more samples, thus increasing procedural time and cost.

Another disadvantage with the device described in the '797 patent is that it "cores" all of the tissue from the skin surface to the interior biopsy site. The device does not permit sampling only at the target location and therefore results in removing healthy tissue.

U.S. Pat. No. 4,682,606 discloses a biopsy apparatus which utilizes a corkscrew mechanism to hold tissue and allow guidance of a cutting instrument which will excise the tissue. The corkscrew mechanism includes a hollow shaft through which a guide extension rod and guided needle can be inserted. The cutting instrument severs the tissue around the area of the corkscrew. This is accomplished by closing a jaw like mechanism at the distal end of the cutting instrument. In addition to the disadvantage of limited sampling as described in connection with the '797 patent above, this particular device also suffers from the disadvantage in that it only allows superficial sampling of the tissue.

U.S. Pat. No. 5,047,040 discloses an atherectomy device and method for removing stenosis material from a vessel by inserting a rotating helical auger shaped bit along a guide wire. An outer tubular cutting member is advanced so that the stenosis is severed and entrapped between the cutter and the bit. U.S. Pat. No. 5,078,723 discloses an atherectomy device for removing stenosis from arteries. A catheter body is used to deliver a stenosis to the cutter site. A screw mounted on the distal end of the body enters and holds the stenosis. An annular cutting means is moved forward around the screw to cut the stenosis which is held by the screw. The catheter is then removed with the cut stenosis trapped inside the cutter. The devices described in these patents again are limited in the sample size which can be taken, and also are restricted to the removal of tissue for limited applications such as removing stenosis material from a vessel. These devices would not be adaptable for other applications where it is desired to remove a targeted tissue mass, for example, in the breast to obtain a breast biopsy.

In view of the increasing demand for a surgical instrument to capture tissue samples for biopsy in a minimally invasive manner while concurrently excising an appropriately sized targeted tissue mass, a surgical instrument for obtaining tissue biopsies for multiple applications is needed. In particular, what is needed is a minimally invasive biopsy instrument which can readily excise a large tissue sample within the targeted tissue mass.

SUMMARY OF THE INVENTION

The invention is a surgical instrument for excising a targeted tissue mass to be biopsied from adjacent bodily tissue on a surgical patient. The instrument comprises an elongated tube and a tissue penetrating spiral.

The elongated tube of the instrument has proximal and distal ends. When the instrument is positioned to excise the targeted tissue mass, the proximal end of the elongated tube is positioned externally of the surgical patient and the distal end of the elongated tube is positioned adjacent the targeted tissue mass.

The tissue penetrating spiral has a spiral lumen therethrough. The spiral is mounted within the elongated tube for rotational movement within the elongated tube.

When the distal end of the elongated tube is positioned adjacent the targeted tissue mass and the spiral is rotated, the spiral penetrates distally into the targeted tissue mass. The targeted tissue mass or a portion of it is received in the spiral lumen to facilitate excising the targeted tissue mass or the portion of it to be biopsied from the adjacent bodily tissue.

The spiral lumen through the tissue penetrating spiral rotatably mounted within the elongated tube of the surgical instrument of this invention provides ample space for receiving a large biopsy sample when targeted tissue is excised from the surgical patient. The sample size obtained can be greater than that from a conventional biopsy instrument which has a lateral tissue receiving port to receive tissue. Importantly, the sample size obtained can be significantly greater than that obtained from instruments designed to excise tissue which have helical threads or corkscrews. Since the tissue sample obtained using the surgical instrument of this invention can be entrapped within the spiral lumen of the tissue penetrating spiral and subsequently severed from adjacent bodily tissue, a larger biopsy sample can be provided in comparison to other biopsy devices.

In a particularly preferred embodiment, the tissue penetrating spiral is removable from the elongated tube when the targeted tissue mass or a portion of the mass has been received in the spiral lumen. In this manner, the excised tissue can be removed from the spiral following removal of the spiral from the elongated tube, and the elongated tube can remain stationary at the surgical site for subsequent re-insertion of the spiral into the elongated tube for taking additional samples as needed or desired.

The surgical instrument of this invention can be used in any surgical procedure where it is necessary or desirable to excise a targeted tissue mass for subsequent biopsy of the excised mass. In particular, it is especially advantageous to use the surgical instrument of this invention when a minimally invasive approach to biopsy is desired, and a sufficiently sized tissue sample is desired to be taken.

DETAILED DESCRIPTION OF THE PREFERRED EMBODIMENTS

Figure 1:
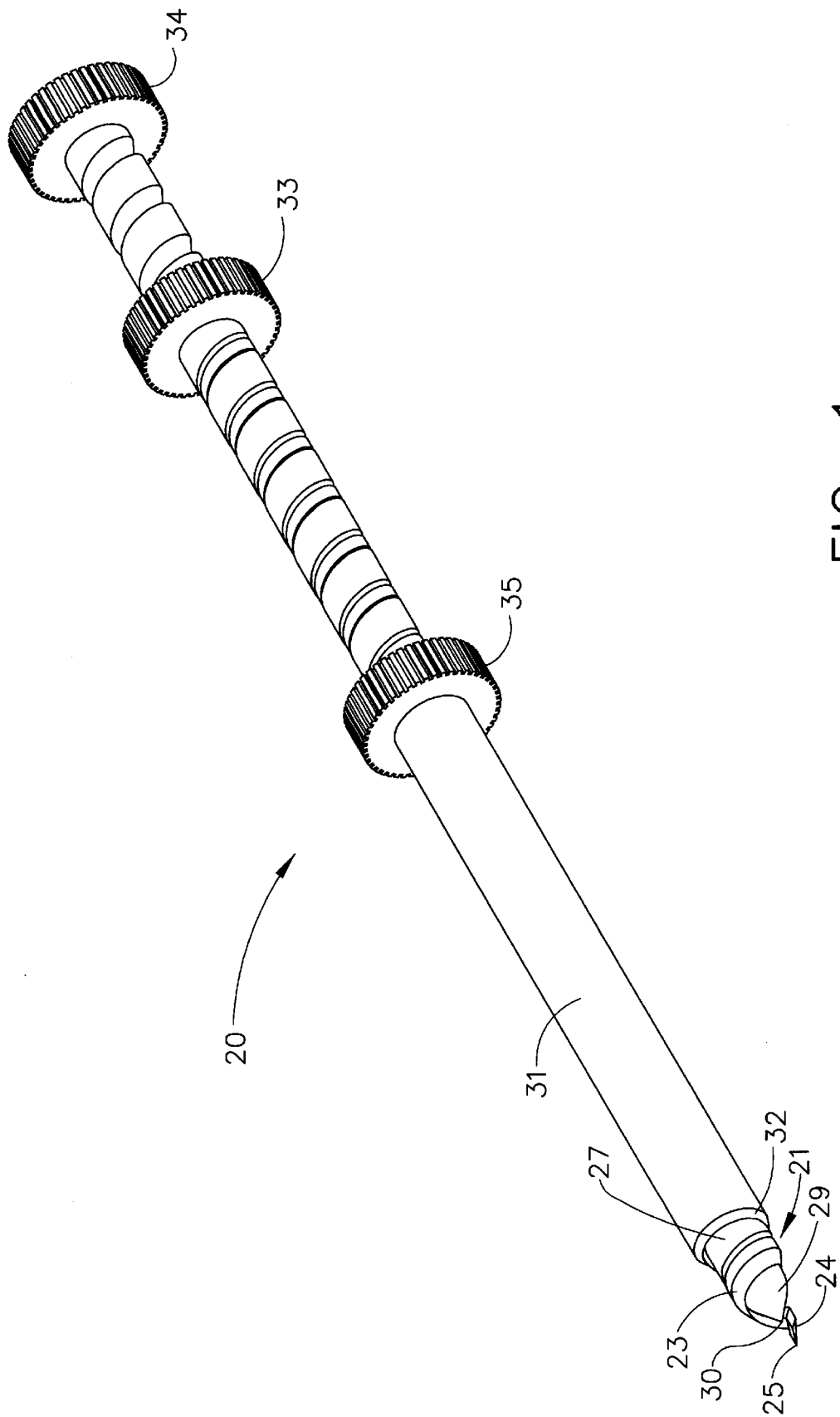
FIG. 1 is an isometric view of a surgical biopsy instrument constructed in accordance with a preferred embodiment of this invention.
Figure 3:
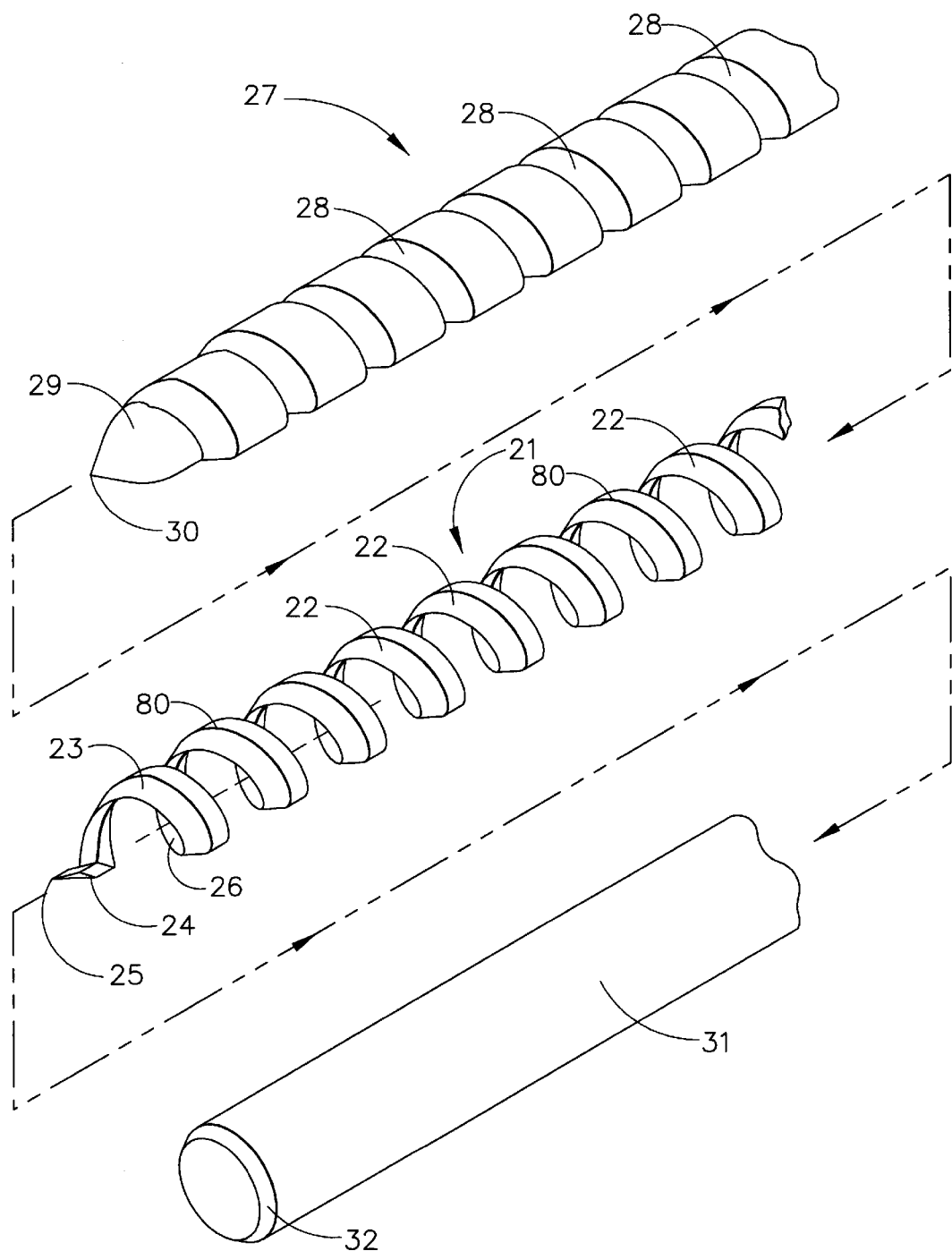
FIG. 3 is an enlarged exploded view of the distal end portions of the spiral biopsy instrument of FIG. 1.
Figure 4:
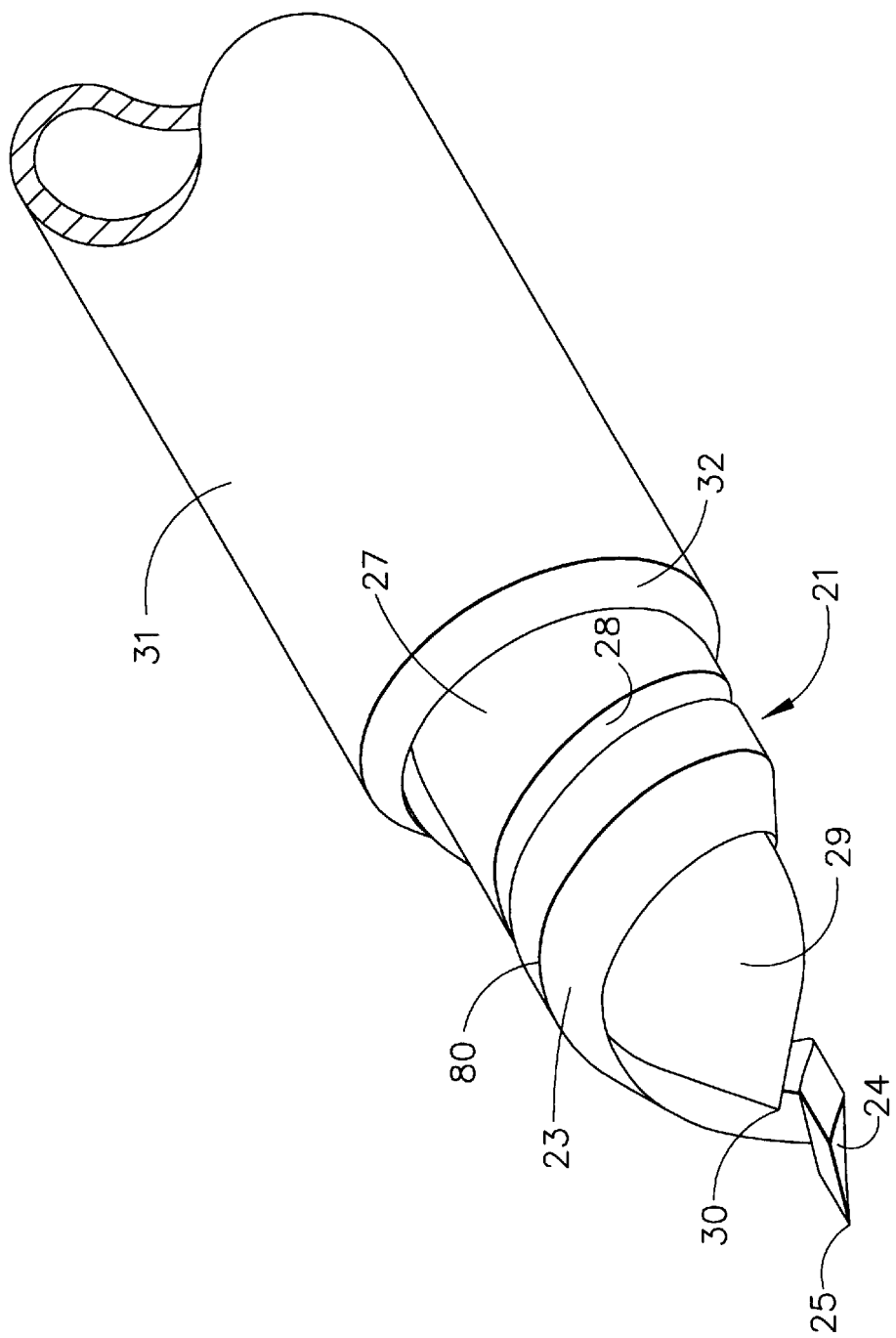
FIG. 4 is an enlarged view in assembly of the distal end portion of the preferred embodiment of the biopsy instrument of FIG. 1.
Figure 5:
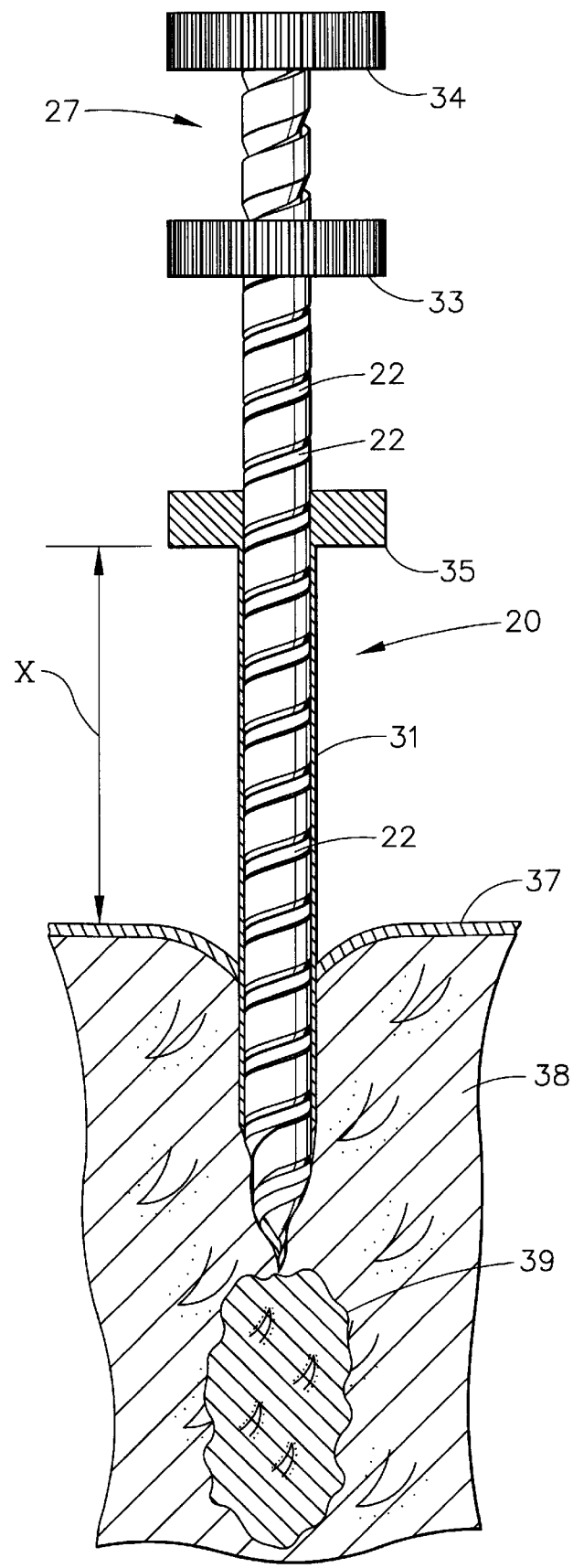
FIG. 5 is a view partially in section of the biopsy instrument of FIG. 1 with its distal end adjacent the targeted tissue mass. The tube handle of the elongated tube is consequently placed at a distance "X" from the surface of the breast.

Referring to FIGS. 1, 3 and 4, there is illustrated the surgical instrument 20 for excising a targeted tissue mass to be biopsied. The biopsy surgical instrument has a long, generally cylindrically shaped penetrating spiral 21. The spiral has a plurality of spaced-apart circular spiral turns 22. As denoted in FIG. 4, the diameter of the penetrating spiral adjacent the distal-most spiral turn 23 decreases until it converges at the distal spiral tip 24. The tip is positioned generally parallel to the longitudinal axis of the penetrating spiral and on or adjacent the centerline of that longitudinal axis. The distal spiral tip 24 has a sharp point 25 to facilitate penetration into tissue. The spiral also has a sharp edge surface 80 extending along substantially its entire length, including the distal spiral tip. The sharp edge surface further facilitates penetration into tissue and, significantly, excision of the biopsy sample. Importantly, a spiral lumen 26 is created within the spiral turns of the penetrating spiral for receiving the tissue desired to be excised and biopsied.

A long, cylindrical spiral core 27 is received within the spiral lumen of the penetrating spiral. The spiral core has a plurality of spiral grooves 28 which are adapted to receive the corresponding spiral turns of the penetrating spiral when the spiral core is loaded into the spiral lumen. The spiral core also has a distal core tip 29 to facilitate entry and penetration into and through the targeted tissue mass. As denoted in FIG. 4, when the spiral core is fully loaded into the spiral lumen, the distal core tip of the spiral core protrudes from the distal-most spiral turn 23, and is positioned between the distal-most spiral turn and the distal spiral tip 25.

Once the spiral core is received into the spiral lumen of the penetrating spiral, the penetrating spiral is loaded into an elongated tube 31 so that the distal-most spiral turn and distal spiral tip protrude from the distal end of the tube. The outer diameter of the penetrating spiral matches the inner diameter of the elongated tube to provide a friction fit. The distal end of the elongated tube has a cutting edge surface 32 for excising tissue which is received in the spiral lumen of the penetrating spiral.

Referring specifically to FIG. 1, the penetrating spiral has a knurled spiral handle 33 at its proximal end. Likewise, the spiral core has a knurled core handle 34 at its proximal end. Further, the elongated tube has a knurled tube handle 35 at its proximal end. The handles of the instrument facilitate the manipulation of the instrument during the biopsy procedure. Specifically, rotation of the spiral and core handles rotates the penetrating spiral and spiral core respectively relative to the elongated tube. Axial movement of the tube handle moves the elongated tube axially relative to the penetrating spiral core.

Figure 2:
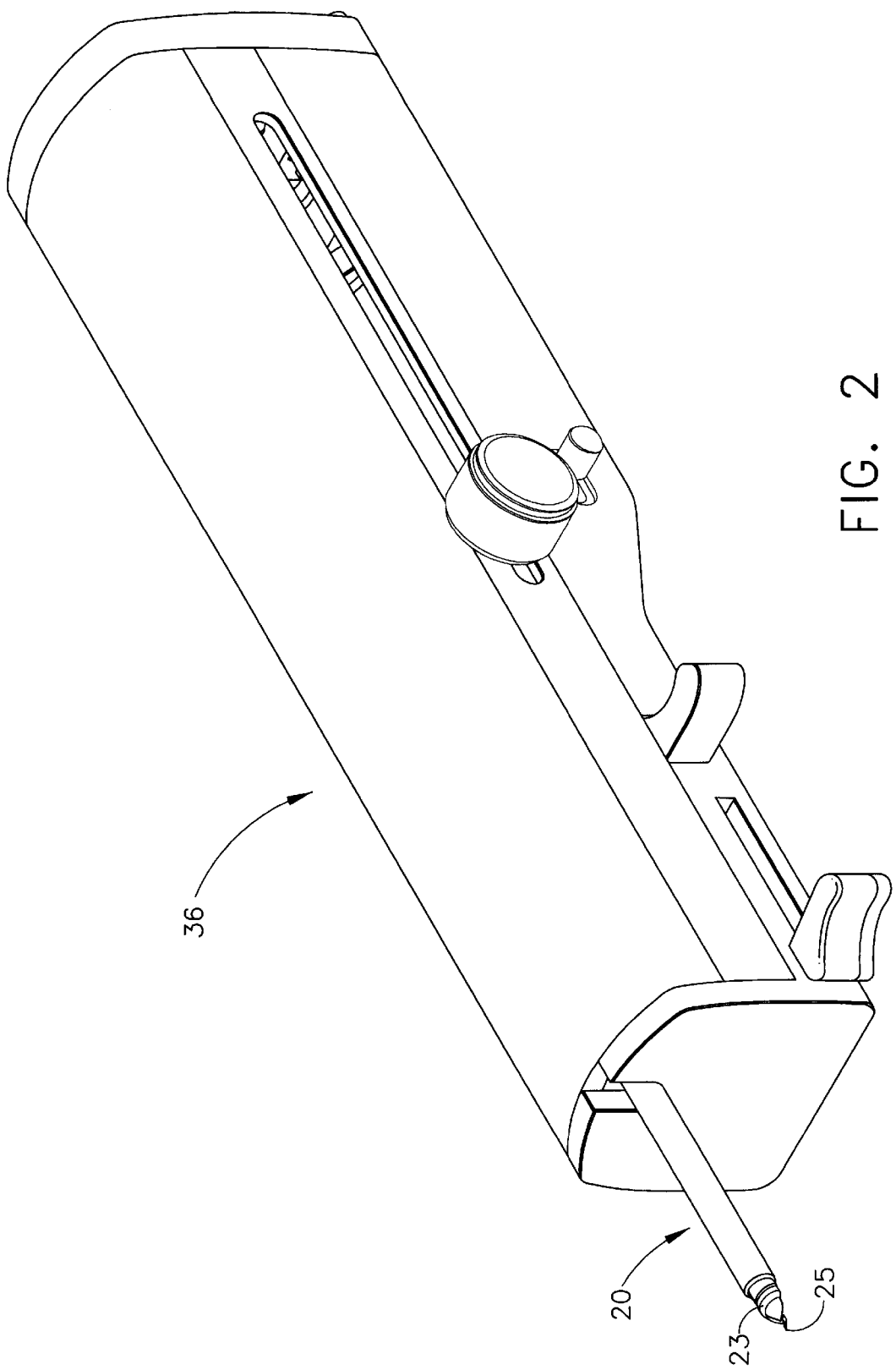
FIG. 2 is an isometric view of an alternate embodiment of the biopsy instrument of FIG. 1 and shown in working relationship with a biopsy holder/driver assembly.

Referring briefly to FIG. 2, the surgical biopsy instrument 20 may be modified so that it can be placed in a drive assembly 36 for the instrument to perform the manipulations of the handles for the penetrating spiral, spiral core and elongated tube. Such a drive assembly for carrying out these manipulations would be conventional to those skilled in this art.

Figure 6:
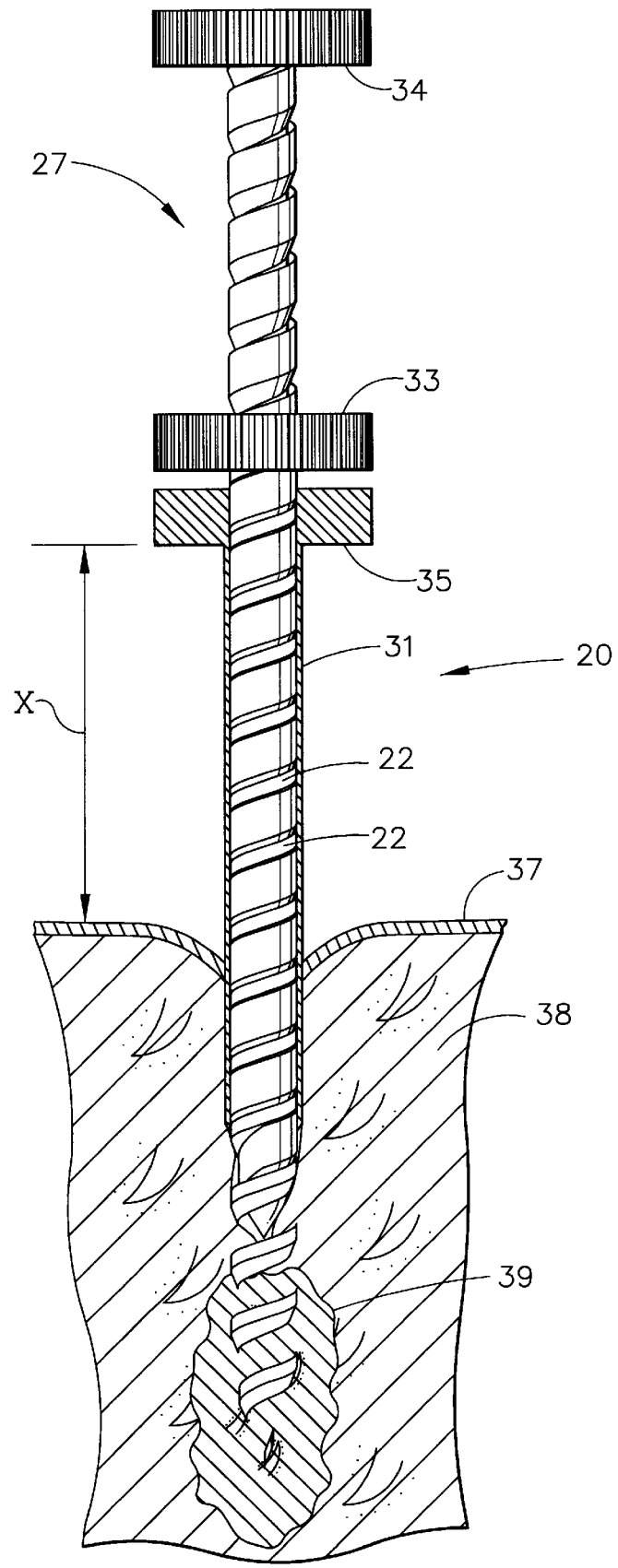
FIG. 6 is a view partially in section of the biopsy instrument of FIG. 1 with its penetrating spiral advanced into the targeted tissue mass.
Figure 7:
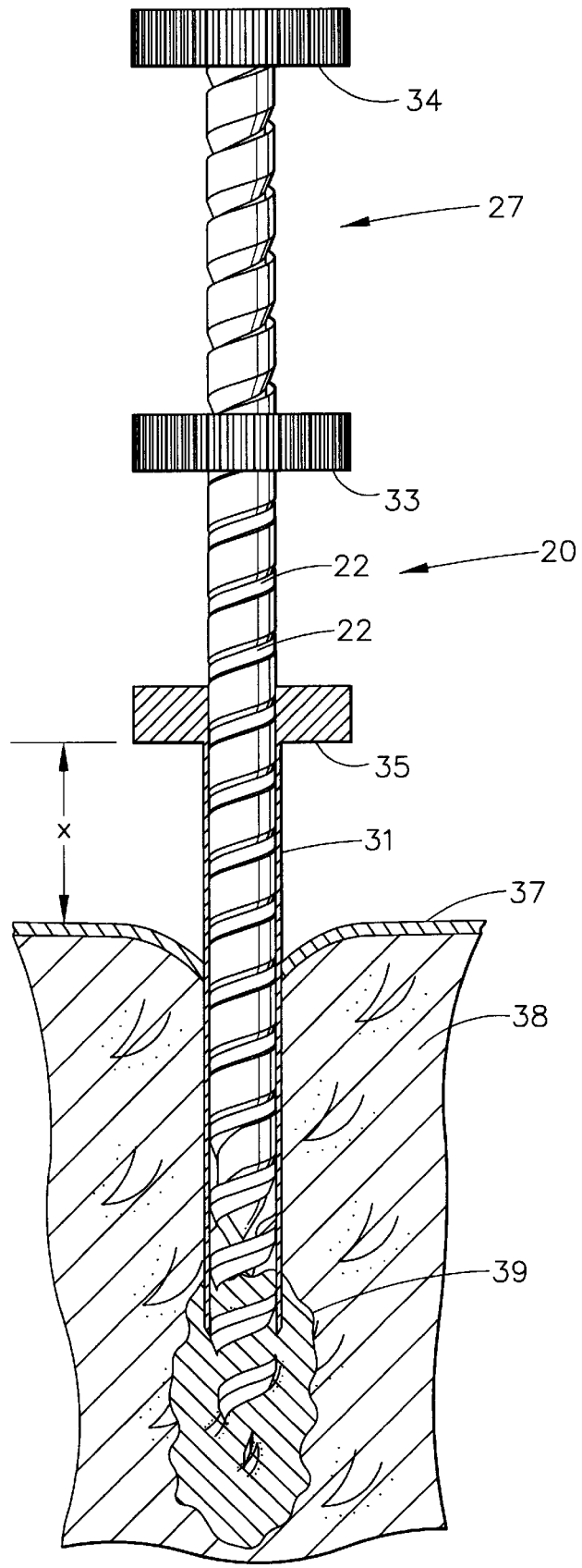
FIG. 7 is a view partially in section of the biopsy instrument of FIG. 1 with its elongated tube advanced in the distal direction to within a distance "x" of the patient, thereby severing the length of the intended tissue sample.
Figure 8:
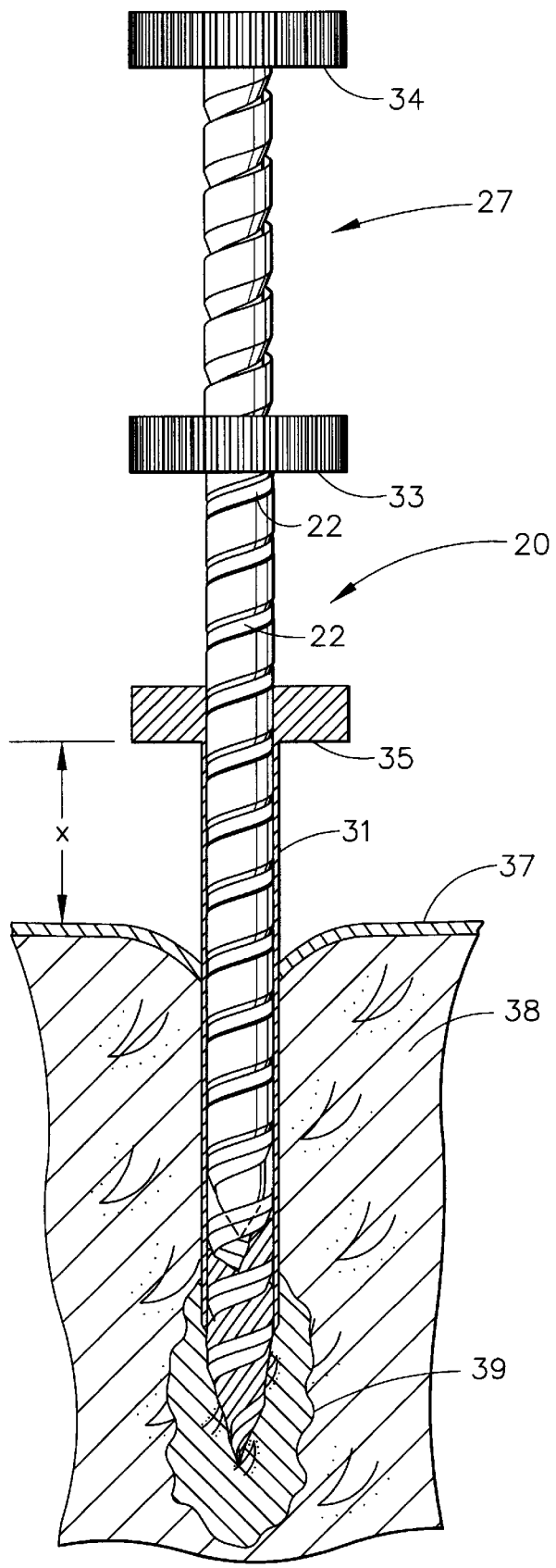
FIG. 8 is a view partially in section of the biopsy instrument of FIG. 1, with its spiral core and penetrating spiral having been rotated in unison to sever the distal end of the intended tissue sample.
Figure 9:
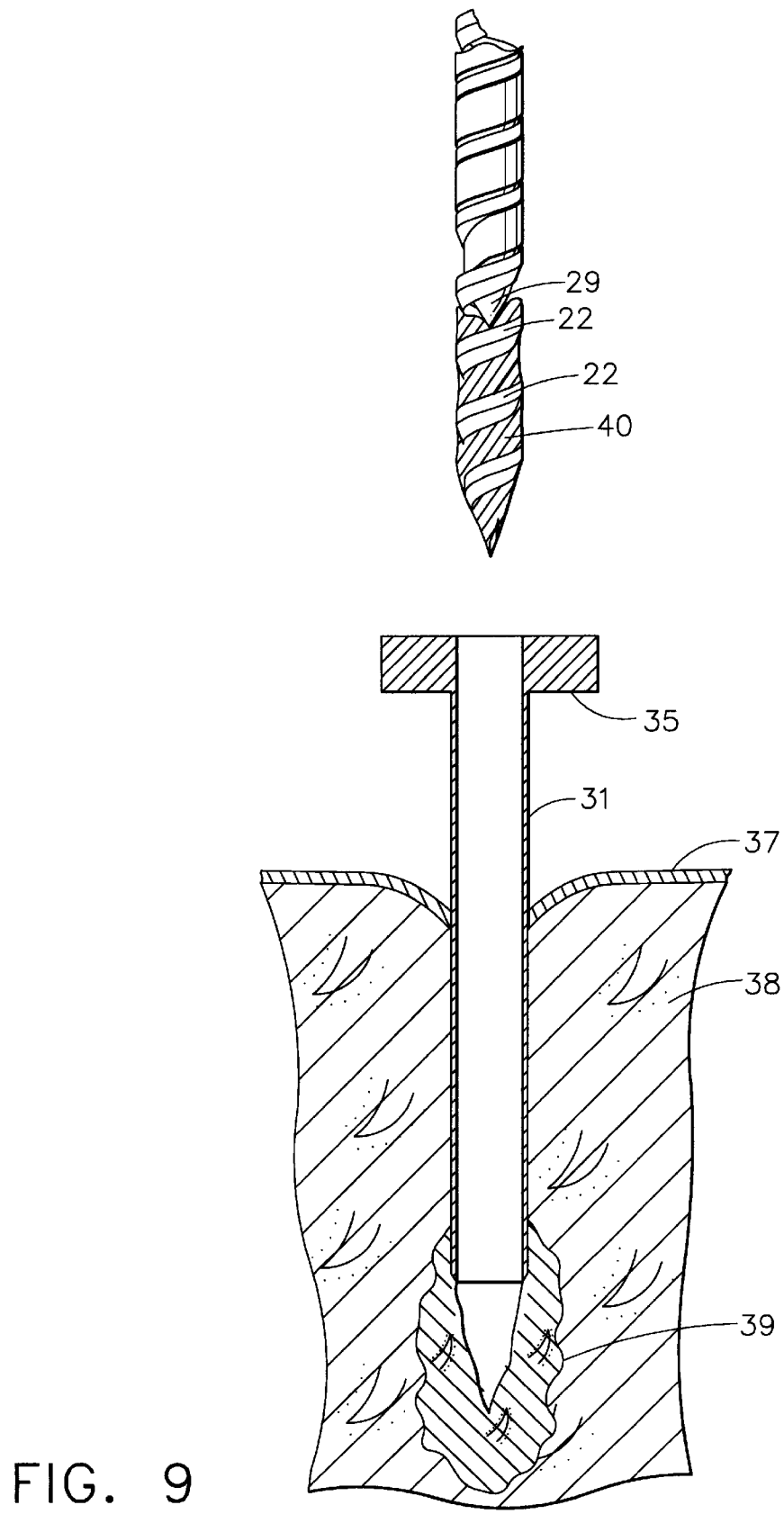
FIG. 9 is a view in section of the biopsy instrument with its spiral core and penetrating spiral having been removed with the sample of the targeted tissue mass contained in the distal end thereof.
Figure 10:
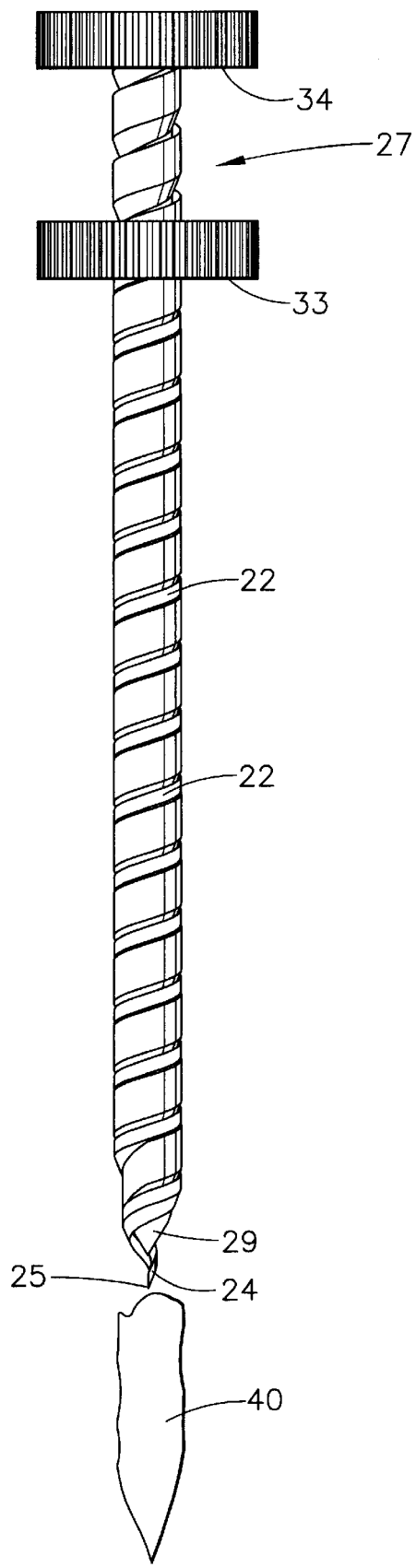
FIG. 10 is an elevation view of the penetrating spiral of the instrument of FIG. 1 having been counter rotated upon the spiral core to its start position, thus releasing the tissue.
Figure 11:
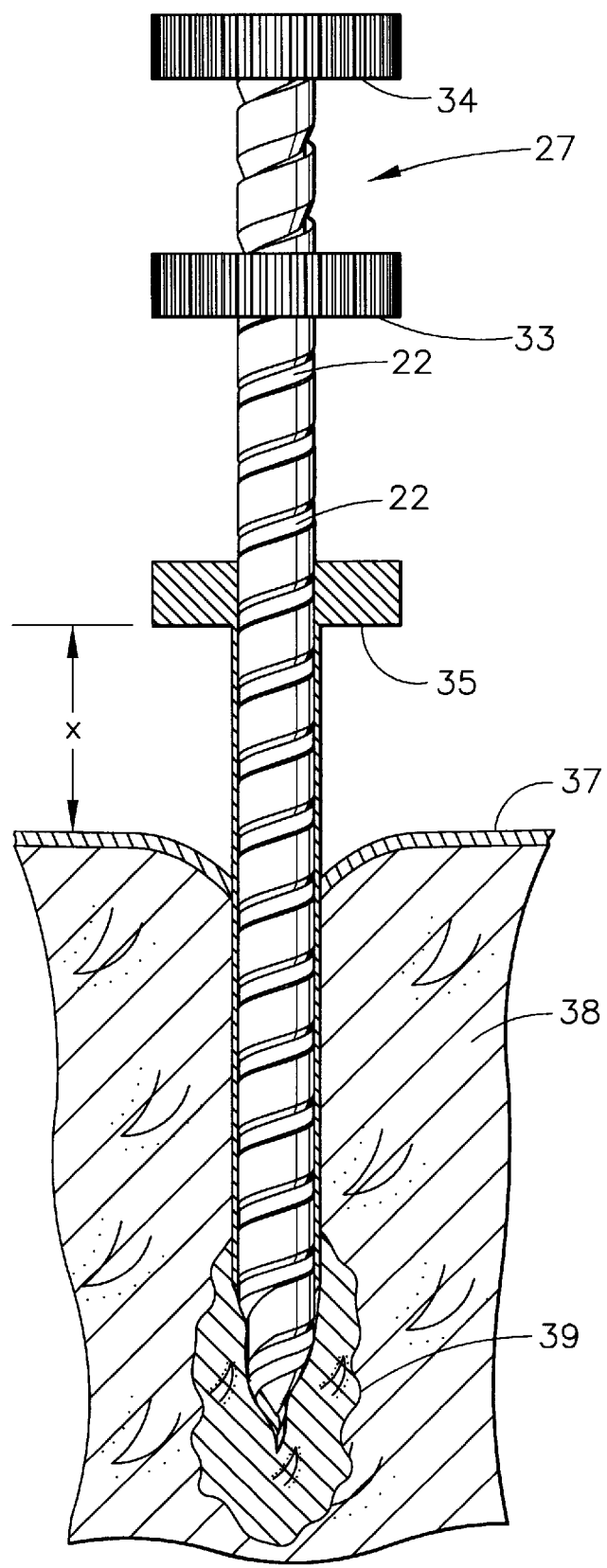
FIG. 11 is an elevation view partially in section illustrating reinsertion of the penetrating spiral and spiral core of the instrument of FIG. 1 into the elongated tube of the biopsy instrument in preparation for taking another tissue sample. The elongated tube was advanced in the distal cutting step and therefore resides at a deeper position in the breast tissue. A distance "X" remains for further penetration.

Referring now to FIGS. 5–11, the sequence of steps illustrating the use of the biopsy surgical instrument is illustrated. The fully assembled instrument is initially inserted through the skin 37 and subcutaneous tissue 38 adjacent the targeted tissue mass 39 to be biopsied. In this position, the proximal end of the elongated tube is positioned externally of the surgically patient, and the distal end of the elongated tube is positioned adjacent the targeted tissue mass. The overall multiple sample length which can be taken from the targeted tissue mass is designated in FIGS. 5 and 6 as "X". Referring now to FIG. 6, downward pressure is exerted on the spiral handle as the spiral handle is rotated to cause the penetrating spiral to penetrate into the target tissue mass. Once the penetrating spiral is positioned within the targeted tissue mass to the desired depth, the elongated tube is moved distally by applying a downward pressure on the tube handle. As the elongated tube moves distally, the distal cutting edge of the tube severs the adjacent tissue surrounding the penetrating spiral from the tissue contained within the spiral lumen. The remaining sample length which can be excised from the targeted tissue mass is denoted in FIGS. 7 and 8 as "x". Referring now specifically to FIG. 8, following excision of the tissue by distal movement of the elongated tube, the spiral and core handles are rotated in unison for removal of the penetrating spiral and spiral core from the elongated tube. In FIG. 9, the reader can observe that the excised tissue 40 has been removed from the elongated tube and the patient, and is contained in the spiral lumen at the distal end of the penetrating spiral. In FIG. 10, the core handle has been counter rotated relative to the spiral handle for distal movement of the spiral core relative to the penetrating spiral. In this manner, the excised tissue 40 is ejected from the spiral lumen, and the spiral core has been returned to its "start" position within the lumen of the penetrating spiral. Finally, when the surgical biopsy instrument is reinserted into the targeted tissue mass, the reader will observe as depicted in FIG. 11 that the instrument can be advanced to a greater depth within the target tissue mass (see the distance denoted as "X" in FIG. 11 versus the similar distance in FIGS. 5 or 6).

Figure 12:
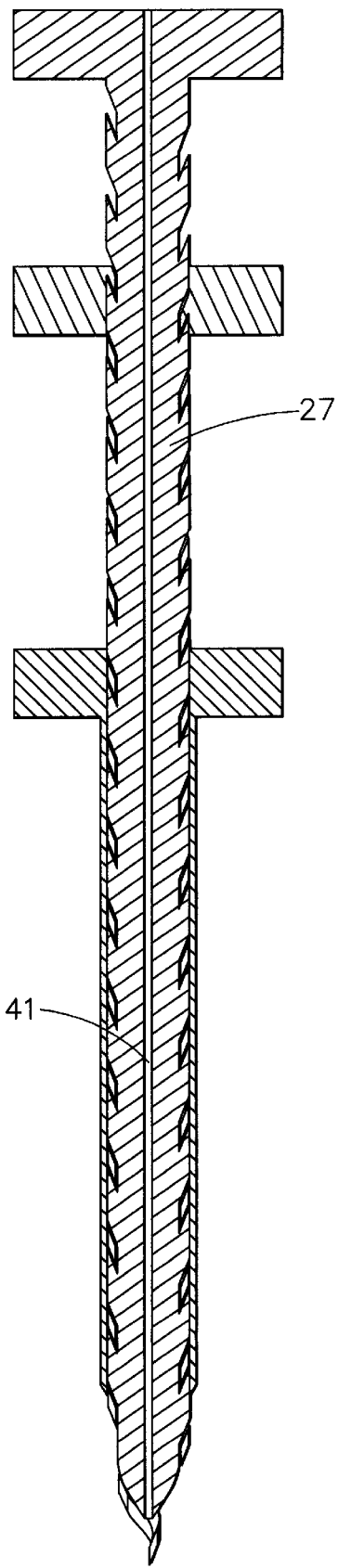
FIG. 12 is the biopsy instrument of FIG. 5 incorporating a central lumen through its spiral core.
Figure 13:
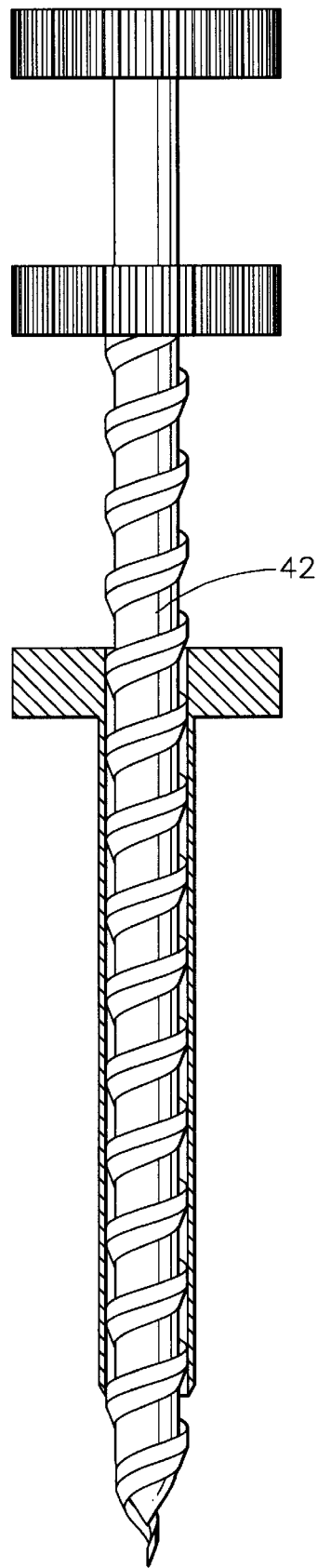
FIG. 13 is the biopsy instrument of FIG. 5 incorporating a smooth core rod.

In another embodiment of this invention depicted in FIG. 12, the spiral core 27 can contain a central guidewire lumen 41 for receiving a guidewire. A guidewire may assist in the precise positioning of the instrument during the biopsy procedure. In another embodiment depicted in FIG. 13, a smooth core rod 42, without grooves, is used to receive the spiral turns is used instead of the spiral core depicted most specifically in FIG. 3.

This invention has been described in connection with its most preferred embodiments. These embodiments are for illustration purposes only, and the invention is not limited to these specific embodiments. Numerous additional embodiments within the scope of the invention will be readily apparent to those skilled in this art. The scope of the invention is defined by the claims which follow.

What is claimed is:

1. A surgical instrument for excising a targeted tissue mass to be biopsied from adjacent bodily tissue on a surgical patient, said instrument comprising:
   a) an elongated tube having proximal and distal ends, and when said instrument is positioned to excise the targeted tissue mass, the proximal end of said elongated tube is positioned externally of the surgical patient and the distal end of said elongated tube is positioned adjacent the targeted tissue mass;
   b) a tissue penetrating spiral having a spiral lumen therethrough, said spiral mounted within said elongated tube for rotational movement therein; and
   c) a spiral core received within said spiral lumen, said spiral core having a plurality of spaced-apart spiral grooves thereon;
wherein when the distal end of said elongated tube is positioned adjacent the targeted tissue mass and said spiral is rotated, said spiral penetrates distally into the targeted tissue mass and the targeted tissue mass or a portion thereof is received in said spiral lumen to facilitate excising the targeted tissue mass or the portion thereof to be biopsied from the adjacent bodily tissue.

2. The instrument of claim 1 wherein the distal end of said elongated tube has a cutting edge surface.

3. The instrument of claim 2 wherein when said spiral has been rotated for penetration into the targeted tissue mass, said elongated tube is movable distally relative to said spiral to excise the targeted tissue mass or the portion thereof received within said spiral lumen from the adjacent bodily tissue with said cutting edge surface of said elongated tube.

4. The instrument of claim 3 wherein said spiral core received within said lumen of said spiral has a distal core tip extending from the distal end of said elongated tube for facilitating the insertion of the distal end of said elongated tube into the surgical patient adjacent the targeted tissue mass.

5. The instrument of claim 4 wherein said spiral core is removable from said lumen of said spiral when the distal end of said elongated tube is positioned adjacent the targeted tissue mass.

6. The instrument of claim 1 wherein said spiral is removable from said elongated tube when the targeted tissue mass or the portion thereof has been received in said spiral lumen.

7. The instrument of claim 6 wherein said spiral has a central guidewire lumen therethrough for receiving a guidewire.

8. The instrument of claim 4 wherein said spiral has a plurality of space-apart spiral turns, and when said spiral core is received in said lumen of said spiral, said spiral turns are receivable in said spiral grooves of said spiral core.

9. The instrument of claim 8 wherein said spiral has a distal-most spiral turn and a distal spiral tip, and said spiral has a decreasing spiral diameter from said distal-most spiral turn to said distal spiral tip.

10. The instrument of claim 9 wherein said spiral has a longitudinal axis, and said distal spiral tip is oriented substantially parallel to the spiral longitudinal axis.

11. The instrument of claim 9 wherein said spiral has a sharp edge surface thereon.

12. The instrument of claim 9 wherein said elongated tube has an inner tube diameter, and when said spiral is mounted within said elongated tube, a friction fit between said spiral and said elongated tube is provided by the spiral diameter and the inner tube diameter.

13. The instrument of claim 9 wherein when said spiral core is received in said lumen of said spiral, said distal core tip is positioned between said distal-most spiral turn and said distal spiral tip.

* * * * *